United States Patent
Bender et al.

(10) Patent No.: US 10,832,803 B2
(45) Date of Patent: *Nov. 10, 2020

(54) AUTOMATED SYSTEM AND METHOD FOR IMPROVING HEALTHCARE COMMUNICATION

(71) Applicant: INTERNATIONAL BUSINESS MACHINES CORPORATION, Armonk, NY (US)

(72) Inventors: Michael Bender, Rye Brook, NY (US); Rhonda L. Childress, Austin, TX (US); Kim A. Eckert, Austin, TX (US); Minh Q. Pham, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 454 days.

This patent is subject to a terminal disclaimer.

(21) Appl. No.: 15/654,083

(22) Filed: Jul. 19, 2017

(65) Prior Publication Data
US 2019/0026436 A1 Jan. 24, 2019

(51) Int. Cl.
*G16H 10/60* (2018.01)
*G06F 16/907* (2019.01)
(Continued)

(52) U.S. Cl.
CPC ........... *G16H 10/60* (2018.01); *G06F 16/00* (2019.01); *G06F 16/68* (2019.01); *G06F 19/324* (2013.01);
(Continued)

(58) Field of Classification Search
CPC ........ G16H 10/60; G16H 40/20; G06F 16/00; G06F 19/324; G06F 19/328; G06F 19/00; G06Q 50/22; G06Q 10/00
See application file for complete search history.

(56) References Cited

U.S. PATENT DOCUMENTS 6,071,236 A 6/2000 Iliff
6,475,143 B2 11/2002 Iliff
(Continued)

FOREIGN PATENT DOCUMENTS

CN 1881415 A 12/2006
CN 101789990 A 7/2010
CN 102063461 A 5/2011

OTHER PUBLICATIONS

Friedman, Jack P.; List of IBM Patents or Patent Applications Treated as Related; Nov. 30, 2017; 1 page.
(Continued)

*Primary Examiner* — Michael Tomaszewski
*Assistant Examiner* — Mohmad Muqueeth
(74) *Attorney, Agent, or Firm* — Schmeiser, Olsen & Watts; Mark C. Vallone

(57) ABSTRACT

Systems, methods and tools for improving healthcare communication between physicians and patients by utilizing audio recordings systems capable of collecting voice data of patient conversations with healthcare providers. The communication system converts the recorded voice data into text using voice to text conversion software, analyzes the voice data using a natural language processor to parse for key words and phrases relating to the patient's health and concerns. Voice data may be additionally analyzed by cognitive analysis systems and machine learning algorithms designed to identify the sentiment that the patient is portraying while discussing the patient's concerns about health-related experiences or symptoms and cross-referenced with social media and other external websites or applications, confirming a patient's sentiment or providing additional key words and phrases unraised by the patient when communicating with the physician.

14 Claims, 12 Drawing Sheets

(51) Int. Cl.

| | | |
|---|---|---|
| *G16H 80/00* | (2018.01) | |
| *G16H 15/00* | (2018.01) | |
| *G16H 40/20* | (2018.01) | |
| *G06F 16/00* | (2019.01) | |
| *G06F 19/00* | (2018.01) | |
| *G06Q 50/22* | (2018.01) | |
| *G06Q 10/00* | (2012.01) | |
| *G06F 16/68* | (2019.01) | |
| *G16H 50/20* | (2018.01) | |

(52) U.S. Cl.
CPC ........... *G06F 19/328* (2013.01); *G06Q 50/22* (2013.01); *G16H 40/20* (2018.01); *G16H 50/20* (2018.01); *G16H 80/00* (2018.01); *G06F 19/00* (2013.01); *G06Q 10/00* (2013.01)

(56) References Cited

U.S. PATENT DOCUMENTS

| | | |
|---|---|---|
| 7,257,531 B2 | 8/2007 | Holub |
| 7,420,472 B2 | 9/2008 | Tran |
| 7,436,311 B2 | 10/2008 | Rapaport et al. |
| 7,533,030 B2 | 5/2009 | Hasan et al. |
| 8,348,839 B2 | 1/2013 | Sharda et al. |
| 2004/0122706 A1 | 6/2004 | Walker et al. |
| 2009/0164237 A1 | 6/2009 | Hunt et al. |
| 2014/0194082 A1* | 7/2014 | Wingert ................ H04W 76/50 455/404.1 |
| 2015/0046189 A1* | 2/2015 | Dao ...................... G06Q 10/10 705/3 |
| 2015/0281853 A1* | 10/2015 | Eisner ................. H04R 25/505 381/312 |
| 2017/0262950 A1* | 9/2017 | Ito ....................... G06F 16/3344 |
| 2017/0329762 A1* | 11/2017 | Lintz .................. H04N 21/2747 |

OTHER PUBLICATIONS

Levit, L. et al. (editors); NCBI Bookshelf, a service of the National Library of Medicine, National Institutes of Health; Committee on Improving the Quality of Cancer Care: Addressing the Challenges of an Aging Population; Board on Health Care Services; Institute of Medicine; Delivering High-Quality Cancer Care: Charting a New Course for a System in Crisis; Dec. 27, 2013; 41 pages.

Notification of Transmittal of the International Search Report and the Written Opinion of the International Searching Authority, or the Declaration; International application No. PCT/IB2018/055135; Applicant's or agent's file reference END170137; dated Nov. 14, 2018; 9 pages.

* cited by examiner

ABSTRACT# AUTOMATED SYSTEM AND METHOD FOR IMPROVING HEALTHCARE COMMUNICATION

BACKGROUND

The present invention relates to data collection, data analytics, and more specifically to embodiments of automated healthcare communication systems.

Healthcare patients often have trouble communicating healthcare concerns with doctors diagnosing and treating the patients. The lack of effective communication is partially due to limited face time doctors have with each patient and the high number of patients that a doctor communicates with on any given day. Often, Information that is given to a doctor's assistant may be lost or misinterpreted by the assistant.

SUMMARY

A first embodiment of the present disclosure provides a method for automating healthcare communication comprising the steps of recording, by a processor of a computing system, voice data of a patient; converting, by the processor, the voice data to text; parsing, by the processor, the text of the voice data for key words; analyzing, by the processor, the voice data for sentiment and stress variables indicating a heightened stress of the patient; ranking, by the processor, the key words as a function of the sentiment and stress variables analyzed; and generating, by the processor, a list corresponding to the ranking of the key words.

A second embodiment of the present disclosure provides a computer system comprising a processor; a memory device coupled to the processor; an audio recording system; and a computer readable storage device coupled to the processor, wherein the storage device contains program code executable by the processor via the memory device to implement a method for automating healthcare communication comprising the steps of: receiving, by the processor of a computing system, voice data of a patient recorded by the audio recording device; converting, by the processor, the voice data to text; parsing, by the processor, the text of the voice data for key words; analyzing, by the processor, the voice data for sentiment and stress variables indicating a heightened stress of the patient; ranking, by the processor, the key words as a function of the sentiment and stress variables analyzed; and generating, by the processor, a list corresponding to the ranking of the key words.

A third embodiment of the present disclosure provides a computer program product comprising a computer readable hardware storage device storing a computer readable program code, the computer readable program code comprising an algorithm that when executed by a computer processor of a computing system implements a method for automating healthcare communication, the method comprising the steps of: receiving, by a processor of a computing system, voice data of a patient recorded by a voice recording system; converting, by the processor, the voice data to text; parsing, by the processor, the text of the voice data for key words; analyzing, by the processor, the voice data for sentiment and stress variables indicating a heightened stress of the patient; ranking, by the processor, the key words as a function of the sentiment and stress variables analyzed; and generating, by the processor, a list corresponding to the ranking of the key words.

A fourth embodiment of the present disclosure provides a method for automating healthcare communication comprising the steps of: receiving, by a processor of a computing system, voice data of a patient recorded by an audio recording system; converting, by the processor, the voice data to text; parsing, by the processor, the text of the voice data for key words; further receiving, by the processor, video data of the patient recorded by a video recording system; tagging, by the processor, the video data of the patient with one or more tagged key words; analyzing, by the processor, voice data and video data for sentiment and stress variables indicating a heightened stress of the patient; ranking, by the processor, the key words and tagged key words as a function of the sentiment and stress variables identified during the analyzing step; generating, by the processor, a list corresponding to the ranking of the key words; and displaying, by the processor, the list generated by the processor on a graphical user interface.

A fifth embodiment of the present disclosure provides a computer system comprising: a processor; a memory device coupled to the processor; an audio recording system; a video recording system; and a computer readable storage device coupled to the processor, wherein the storage device contains program code executable by the processor via the memory device to implement a method for automating healthcare communication comprising the steps of: receiving, by a processor of a computing system, voice data of a patient recorded by the audio recording system; converting, by the processor, the voice data to text; parsing, by the processor, the text of the voice data for key words; further receiving, by the processor, video data of the patient recorded by the video recording system; tagging, by the processor, the video data of the patient with one or more tagged key words; analyzing, by the processor, voice data and video data for sentiment and stress variables indicating a heightened stress of the patient; ranking, by the processor, the key words and tagged key words as a function of the sentiment and stress variables identified during the analyzing step; generating, by the processor, a list corresponding to the ranking of the key words; and displaying, by the processor, the list generated by the processor on a graphical user interface.

DETAILED DESCRIPTION

Figure 1:
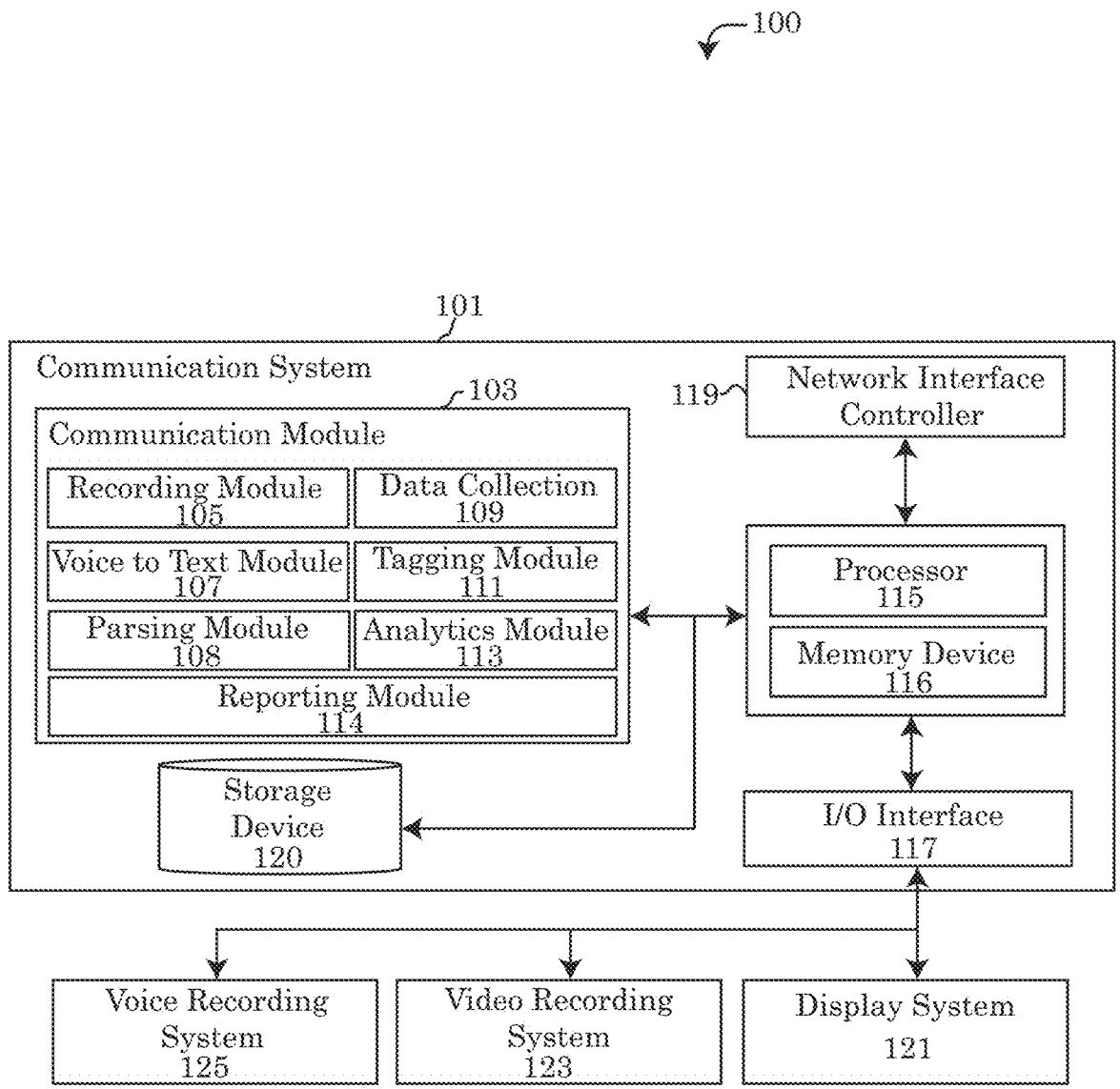
FIG. 1 depicts a block diagram of a healthcare communication system, in accordance with the embodiments of the present invention.

Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure. A more complete understanding of the present embodiments and advantages thereof may be acquired by referring to the following description taken in conjunction with the accompanying drawings, in which like reference numbers indicate like features.

As a preface to the detailed description, it should be noted that, as used in this specification and the appended claims, the singular forms "a", "an" and "the" include plural referents, unless the context clearly dictates otherwise.

Overview

Existing systems for facilitating communication between doctor and patient consist of verbal and electronic communications sent directly between patient and doctor or direct communications between the patient and employees of the doctor, such as nurses, receptionist or physician assistants. Patients often have trouble effectively communicating health concerns to the doctor directly or patients have trouble emphasizing the importance of the patients' concerns, which may render the doctor as appearing uncaring or not listening as carefully as the physician should be. The shortcomings of direct communication may be a result of limited face time that the physician may have with patients or the high volume of patients that the doctor may interact with during any given work day. Simultaneously, information that may be provided to assistants, nurses and employees of the doctor's office or hospital may be forgotten, overlooked or misinterpreted by the recipient and thus result in the doctor never receiving or not fully grasping the importance of the information provided by the patient. Moreover, in some instances, patients may simply not emphasize concerns during face to face time with the doctor. The lack of information or misinterpreted information being communicated about the patient's healthcare may cause the doctors to fail in the identification of informational trends in symptoms or complaints by the patient, ultimately leading to the receipt of inferior healthcare.

Embodiments of the present disclosure improve healthcare communication between doctors, the doctor's employees and the patients, minimizing the effects of underemphasized, lost or misinterpreted details that may have been important for doctors to focus on. Embodiments of the present disclosure provide alternative opportunities for patients' concerns and discussions to be readily analyzed and sent to the doctor even when the doctor is not in the presence of the patient. Embodiments of the present disclosure leverage computer systems engaging in data collection, data analytics, natural language processing, machine learning, cognitive analysis of verbal communications and/or visual cues of body language, to identify, track and emphasize symptoms and concerns of patients that may be important for a healthcare professional to notice.

Embodiments of the healthcare communication systems described herein may utilize audio recordings systems to collect voice data of the patient from numerous discussions that may occur in the presence or absence of the physician, while the patient is within range of the audio recording devices. The audio recording system may include one or more microphones or other types of audio recording devices positioned throughout the healthcare provider's facilities. The microphones and recording devices may capture communications between the patient and the medical office's personnel. The healthcare communication system may convert the recorded voice data into text using voice to text conversion software. The resulting text created from the voice data may be analyzed using a natural language processor, parsed for key words and phrases relating to the patient's health and concerns. The key words and phrases identified may be tabulated to account for the frequency in which the identified key words and phrases are mentioned in the collected voice data, as well as tracking the key words over a period of time in order to determine whether the concerns are reoccurring and/or becoming a bigger concern of the patient.

In some embodiments of the healthcare communication system, voice data may be additionally analyzed by cognitive analysis systems and machine learning algorithms designed to identify the sentiment that the patient is portraying while discussing the patient's concerns about health-related experiences or symptoms. The healthcare communication system may be programmed to detect variables in the human voice that may be indicators of stress or anxiety (stress variables). For example, the system may detect anger, frustration, sadness, fear etc. in the patient's recorded voice data, indicating a heightened level of stress being experienced by the patient as the patient is describing health-related experiences. The stress variables may potentially provide clues to the physician about topics of concern that may require additional focus or emphasis while treating the patient in the future.

Embodiments of the healthcare communication system may rank the key words in order of perceived importance as a function of the frequency in which the key words appear in the voice data and as a function of the stress levels identified by the natural language processor. Key words and topics may be provided to the physician in the form of a report that may be viewed by physician. The report may help to focus the physician's attention and provide a written structure for the physician to follow and address the concerns of the patient. Upon viewing the report comprising the ranked key words and topics, the physician may become aware of potential health concerns that the physician may not have considered as being important for the particular patient. The keywords, concerns and stress levels of the patient may evolve over time. The report generated may be continuously updated over time as the patient's concerns and keywords change, allowing for the healthcare communication system to track a patient's healthcare concerns Embodiments of the healthcare communication system described herein may further amend the rankings of key words and phrases generated in the report provided to the physician with additional data from an external data source. For example, a social media website, application, program or messaging service. The healthcare communication system may scan external data sources for additional information about the patient and supplement the collected voice data to provide additional context of the patient's concerns. For instance, a patient may post numerous times on a social media website about a particular symptom or healthcare concern. The healthcare communication system may parse the patient's posts and consider the content of the posts while analyzing key words of the voice data collected by the audio recording system. Embodiments of the healthcare communication system may factor the data collected from the external data sources when ranking the key words and phrases parsed from the collected audio data in order to gauge the overall importance of a particular topic.

Healthcare Communication System

Referring to the drawings, FIGS. 1-8 illustrate embodiments of a healthcare communication system 100, 200, 300, 400 for automating healthcare communication between patients and physicians, consistent with the disclosures of this application. Embodiments of system 100 may comprise a specialized computer system, referred to as communication system 101. Embodiments of the communication system 101 operating as a specialized computer system may include a processor 115, specialized hardware or circuitry, chipsets and/or software loaded in the memory device 116 of the communication system 101. Embodiments of the communication system 101 may perform one or more functions, tasks or routines relating to the recordation of voice data, converting the voice data to text, parsing the voice data for key words and phrases, accessing contextual data from one or more network accessible data sources 131a, 131b . . . 131n (hereinafter referred to collectively as "data sources 131"), tagging the collected and recorded data with one or more tags, ranking the key words and phrases as a function of importance and generating reports presenting the ranked key words and phrases that may be identified over a specific period of time.

Embodiments of the specialized hardware and/or software integrated into the communication system 101 may be integrated into the communication systems 101 as part of a communication module 103. The communication module 103 may include hardware components and software applications performing each of the functions of the communication system 101, including, but not limited to the recordation of voice data, converting the voice data to text, parsing the voice data, accessing contextual data from data sources 131, tagging the voice data, ranking the key words and phrases and generating reports. As used herein, the term "module" may refer to a hardware module, software-based module or a module may be a combination of hardware and software resources of the communication system 101 and/or resources remotely accessible to the communication system 101 via a network 130.

The hardware and/or software components of the communication system 101 may include one or more sub modules performing one or more specific tasks of the communication system. The sub modules actively performing the tasks of a particular embodiment of the communication system 101 may vary. Examples of sub modules that may be part of the communication module 103 may include a recording module 105, voice to text module 107, parsing module 108, data collection module 109, tagging module 111, analytics module 113 and/or reporting module 114.

Figure 2:
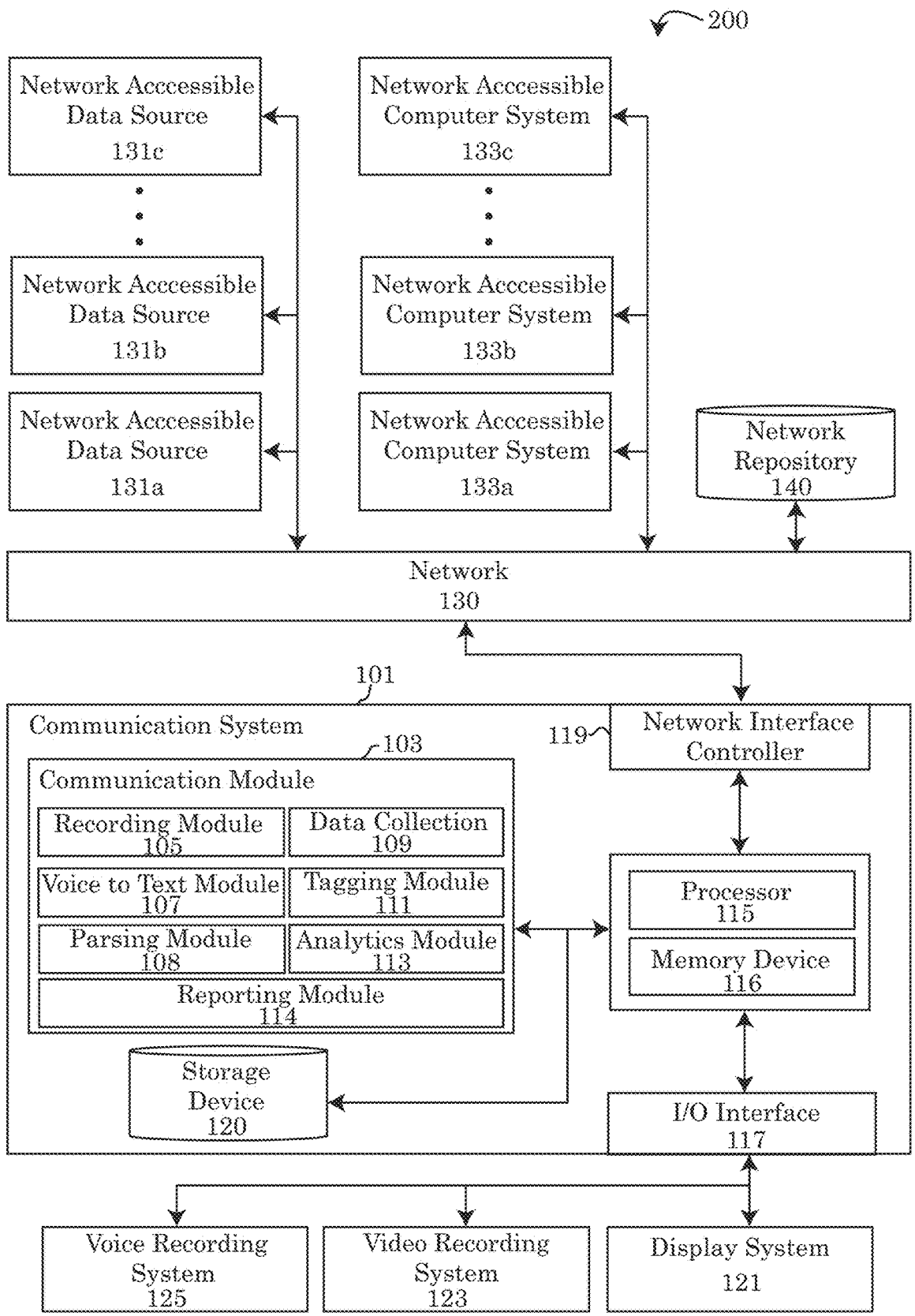
FIG. 2 depicts a block diagram of an alternative embodiment of a healthcare communication system in accordance with the embodiments of present invention.
Figure 3:
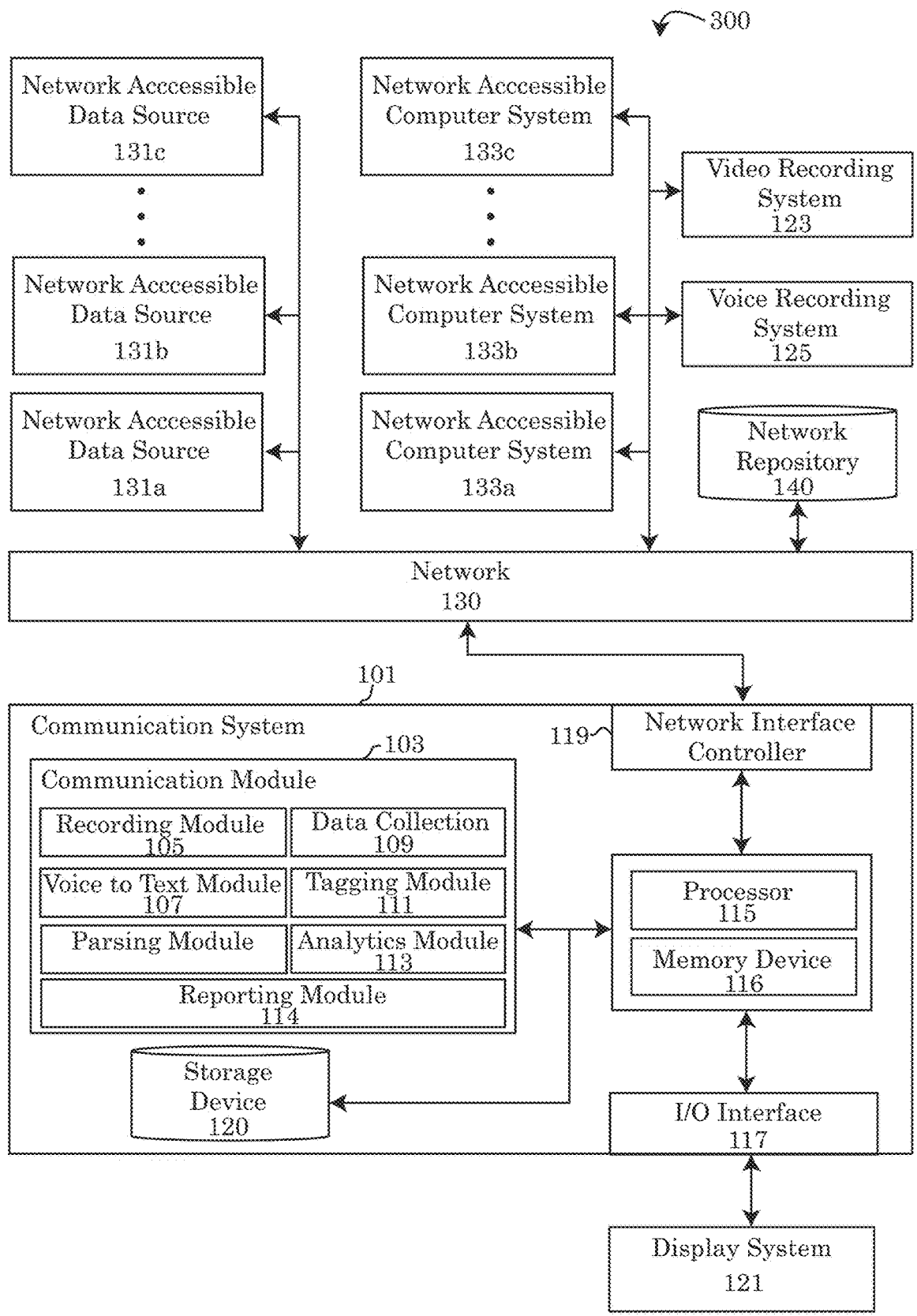
FIG. 3 depicts a block diagram of a second alternative embodiment of a healthcare communication system in accordance with the embodiments of the present invention.

Embodiments of system 100, may include a plurality of computer systems connected and placed in communication with one another over a computer network 130, including one or more network accessible computing devices 133a, 133b . . . 133n (hereinafter referred to collectively as "network accessible computer devices 133"), network accessible repositories 140, voice recording systems 125 or video recording systems 123. Embodiments of the network 130 may be constructed using wired or wireless connections between each hardware component connected to the network 130. As shown in the embodiments of FIGS. 2-3, each of the computer systems 101, 123, 125, 133, 140 may connect to the network 130 and communicate over the network 130, for example using a network interface controller (NIC) 119 or other network communication device. Embodiments of the NIC 119 may implement specialized electronic circuitry allowing for communication using a specific physical layer and a data link layer standard, such as Ethernet, Fiber channel, Wi-Fi or Token Ring. The NIC 119 may further allow for a full network protocol stack, enabling communication over network 130 to the group of computer systems 101, 123, 125, 133, 140 or other computing hardware devices linked together through communication channels.

The network 130 may facilitate communication and resource sharing among the computer systems 101, 123, 125, 133, 140 and additional hardware devices connected to the network 130. Embodiments of the present disclosure are capable of being implemented in conjunction with any type of computing environment now known or later developed. For instance, the network 130 may include a local area network (LAN), home area network (HAN), wide area network (WAN), back bone networks (BBN), peer to peer networks (P2P), cloud computing environment 150, campus networks, enterprise networks, the Internet, and any other network known by a person skilled in the art.

Referring to the drawings, FIG. 1 illustrates a diagram of a healthcare communication system 100 for automating healthcare communication between patient and physician. Embodiments of system 100 may comprise communication system 101. Embodiments of the communication system 101 may be a computing system comprising hardware and software components as depicted in embodiment 100 and in some embodiments, may integrate one or more components of a generic computer system 1100 described in detail below. Embodiments of the communication system 101 may comprise a processor 115, memory device 116, an input/output (I/O) interface 117 and one or more computer readable data storage devices 120 as understood by individuals skilled in the art and in accordance with processors, memory devices, I/O interfaces and computer readable storage devices that may be part of a generic computing system 1100. Embodiments of the communication system 101 may include a communication network module 103 comprising specific hardware modules and/or software modules loaded into the memory device 116.

In some embodiments of the communication system 101, the communication module 103 may include a recording module 105. The recording module 105 may perform the function or task of collecting and retrieving voice data from a voice recording system 125 and/or video data from a video recording system 123 connected to the communication system 101. As shown by the various embodiments of the figures, the voice recording system 125 and video recording system 123 may be connected locally to the communication system via an I/O interface 117 as depicted in embodiments 100, 200. In alternative embodiments, the voice 125 and video recording systems 123 may be connected to the communication system 101 over network 130. In some embodiments of the healthcare communication system 100, 200, 300, 400 the voice recording system 125 may include one or more microphones or digital voice recording devices, whereas the video recording system 123 may include one or more camera system. In some embodiments, the voice recording system 125 and the video recording system 123 may be combined into a single unit comprising a camera and microphone which may record and transmit both voice and video to the recording module 105.

In some embodiments of the healthcare communication system 100, 200, 300, 400, the video recording system 123 and voice recording system 125 may continuously stream video data and voice data to the recording module 105 of the communication module 103. The recording module 105 receiving the voice data and video data may organize and store the voice and video data in one or more local storage devices 120 or network accessible data repositories 140, for further processing and analysis by the communication system 101. In alternative embodiments, the recording module may not always be recording voice and video data, but may instead selectively record voice and video data when vocal sounds initiate the voice recording system 125 and/or movement initiates the video recording system 123. In some embodiments of the communication system, the recording module 105 may include wired or wireless connectivity hardware, such as Wi-Fi, Bluetooth, Bluetooth low energy, infrared, Zigbee, WiMAX or other communication technologies capable of sending and receiving signals between the recording module 105 and the voice recording system and/or video recording system.

Embodiments of the communication module 103 may further comprise a voice to text module. Embodiments of the voice to text module 107 may perform the function of converting voice data received from the voice recording system 125 to computer readable format comprising text. In some embodiments, the voice to text module 107 may convert the voice data collected by the recording module 105 into text by translating an analog wave recorded by the microphone of the voice recording system 125 into digital data via an analog-to-digital converter (ADC). The voice to text module 107 and/or the microphone of the voice recording system 125 may digitize the speech of the patient and or healthcare professionals conversing, by taking measurements of the analog waves produced by speech at a series of intervals. The voice to text module 107 may filter the digitized sound of the recorded voice data to remove unwanted background noise or to separate the sounds into different bands of frequency. The voice to text module 107 may match segments of the recorded voice data to known phenomes of the language recorded by the voice recording system 125. Voice to text module 107 may match phenomes with the context of the other phenomes recorded to create a contextual phenome plot. The contextual phenome plot may be processed through a statistical model comparing the sounds of each phenome in the recorded voice data to a library of known words, phrases and sentences stored by the communication system 101 or a network accessible repository 140. Once the words of the voice data have been identified, the voice data may be outputted as text and stored as a file by the voice to text module 107 for further analysis and processing by the additional sub modules of the communication module 103.

Embodiments of the communication module 103 may include a parsing module 108. The parsing module 108 may perform the task or function of analyzing the text output of the voice to text module 107 for one or more healthcare related key words and phrases. The parsing module may process the text output of the voice to text module 107 by transforming the text into a parse tree or an abstract syntax tree in some embodiments. The parsing of the text, performed by the parsing module 108, may be performed by three different components. The components may include a scanner, lexer and parser. The scanner may read the text being parsed one character at a time. As the scanner reads each character of the text, the scanner may pass the character information to the lexer, which may transform the stream of characters into a stream of tokens. During tokenization, the string of input characters may be classified and passed on to the parser. The parser reads the stream of tokens produced by the lexer and builds a parse tree or syntax tree in accordance with a set of language rules. As the parsing module builds the parse tree or syntax tree, one or more key words or phrases may be identified as important or contextually appropriate to healthcare. Embodiments of the parsing module 108 may track the keywords or phrases relating to healthcare which repeatedly appear in the parsed text as well as track the number of times each of the keywords appear.

In some embodiments, the parsing module 108 may further comprise a natural language processor which may responsible for performing the task of providing a sentiment analysis of the text output received from the voice to text module 107. Sentiment Analysis is the process of determining whether a piece of writing (in this case the outputted text) is positive, negative or neutral. Sentiment analysis may also derive the opinion or attitude of a speaker. The natural language processor may be responsible for systematically identifying the attitude and emotional reaction of the speaker recorded in the voice data, which may provide context to the emotions of a patient conveying health concerns or symptoms. Sentiment analysis may be performed using one or more different methods to characterize the text outputted by the voice tot text module 107. For example, the natural language processor of the parsing module 108 may store a predetermined list of positive and negative words, which may be weighted depending on each words' strength in conveying positive or negative qualities.

In alternative embodiments, sentiment analysis may be performed by the natural language processor using machine learning. Machine learning techniques may rely on the communication system's 101 ability to automatically learn from the language used, expressions of sentiment. Machine learning may be used by first providing training to the natural language processor. For example, by providing sample sets of positive and negative language which may denote particular sentiments and emotions. Numerous examples sets may be provided to the natural language processor during the training phase. The more examples provided, the more accurately the natural language processor may accurately predict the sentiment and emotions conveyed in the text output of the recorded voice data. Once the natural language processor has learned from the examples provided in the training sequence, the natural language processor can apply the acquired knowledge to new and unseen text outputs from the voice tot text module 107 and classify the text into one or more different sentiments.

Moreover, in some embodiments, the natural language processor may additionally be trained to identify various sentiments that may indicate stress in the voice of the recorded individual (i.e. the patient). For example, certain sentiment may be classified as more indicative of stress, such as anger, anxiousness and fright, whereas other sentiments such as happiness and joy may not be indicators of stress.

In some embodiments of the communication systems 101 the accuracy of identifying the stress level and sentiment of the patient from recorded voice data may be improved by further recording and analyzing the body language of the patient while speaking. For example, in some embodiments, the communication system 101 may be placed into electronic communication with a video recording system 123. The video recording system may capture digital video of the patient communicating with healthcare personnel at the same time that voice data is recorded by the voice recording system 125. Video data recorded by the video recording system may be streamed and transmitted to the recording module 105. The video data may be processed by a video analysis module capable of detecting body language through the presentation of hand gestures, specific movements and facial expressions captured in the video data. Similar to the natural language processor, video analysis module may undergo machine learning techniques to properly train the video analysis module about the positive and negative connotations of specific body language.

In some embodiments, the voice data and video data may be encoded with a time stamp. The communication module 103, and more particularly the analytics module (described below) may utilize the encoded time stamp to compare the sentiment analysis of the voice data and the body language of the patient at the time the voice data was provided. The inclusion of both audio and visual analysis of the patient may improve the accuracy of the conclusions drawn about the patient's sentiment when certain key words or phrases regarding healthcare and symptoms are spoken.

Embodiments of the communication system 101 may further cross reference keywords extrapolated from voice data and the sentiment analysis thereof, with other network accessible data sources 131 that may provide additional context and insight into the patient's healthcare concerns. The data collection module 109 may perform the function of retrieving additional data from external data sources available to the communication system over network 130. Network accessible data sources 131 may include, but are not limited to data retrieved from social media profiles, emails, direct messaging services, websites, SMS text messages, recorded phone conversations, etc. For example, the data collection module 109 may retrieve a series of social media posts of a patient's social media profile over a period of time complaining about one or more medical symptoms. Moreover, the data collection module 109 may further scan network accessible data sources 131 for additional changes in a patient's lifestyle that may indicate a medical concern or complaint that a patient may have, indicating that a patient may be suffering from a condition and/or compensating for a condition that the patient may be unaware of. As the communication system 101 compiles areas of concern to present to a physician, the additional data retrieved from network accessible data sources may be used as a cross reference with the keywords parsed from the voice data and/or treated as a separate set of patient information that may be cause for concern by the physician.

In some embodiments of the communication module 103, the communication module may be equipped with a tagging module 111. The tagging module 111 analyze one or more types of data collected by the communication system and input one or metadata tags in the collected data file in order to categorize and classify the collected data. For example, the tagging module may apply one or more tags in the metadata of the voice data, video data, text outputted from the voice to text module 107, the keywords and phrases outputted by the parsing module 108, and the network accessible data sources 131 retrieved by the data collection module 109. The tags applied to the each piece of data generated or collected by the system 100, 200, 300, 400 may describe the data and make it easier for the system 100, 200, 300, 400 to search and query the collected data by tag. Moreover, in some embodiments, the tagging module 111 may further apply date tags to each of the pieces of data collected by the system 100, 200, 300, 400. By applying dates as tags to each of the different types of collected data, the communication system 101 may generate queries between specified date ranges in order to gauge the sentiment and concerns of the patient during different moments in time.

Embodiments of the communication system 101 may comprise an analytics module 113. the data analytics module 113 perform qualitative and quantitative techniques and processes on the data created by the voice recording systems 125, video recording systems 123 and network accessible data sources 131. Using each piece of collected data harvested by the communication system 101, the analytics module 113 may identify patterns to patient behavior and draw conclusions. In particular, the analytic module 113 may identify patterns relating to the patient's healthcare concerns or symptoms.

Embodiments of the analytics module 113 may be responsible for drawing conclusions about each patient's healthcare concerns and ranking the concerns of the patient as a function of keywords' sentiment of the voice data collected, the stress levels associated with the patient's sentiment while communicating the identified keywords and the frequency of the keywords being identified in the parsed voice data. The analytics module may further organize and rank keywords and phrases associated with the voice data as a function of cross referencing the keywords with network accessible data sources comprising comments and indicators of concern about particular keywords, separate from the voice data as well as video analysis of the patient's body language collected by the video recording system 123.

For example, the analytics module 113 may rank keywords or phrases associated with medical symptoms as a higher point of concern for the physician to further focus on when the same or similar keywords appear frequently or repeatedly. Frequently occurring keywords may be ranked higher than keywords that appear less frequently or infrequently. Likewise, keywords or phrases associated with high levels of stress and anxiety may be rated higher keywords that are identified as having a lower level of stress or anxiety in the patient when the keywords are discussed. In some embodiments, the analytics module 113 may rate particular keywords higher in instances where there is repeated discussion by the patient either to non-physicians or socially (i.e. on social media). The analytics system 113 may conclude that the keywords or symptoms not being raised to the physician should be and thus the analytics system may rank undiscussed keywords that may not have been collected as voice data during patient-physician discussions highly in order to focus the physician on addressing the matter directly with the patient.

Embodiments of the communication module 103 may further comprise a reporting module 114. The reporting module 114 may perform the task of generating and/or displaying a list of ranked key words and/or symptoms organized by the analytics module 113 as a function of the voice data, video data and/or network accessible data sources 131. The reporting module 114 may present the ranked list of keywords in a computer readable format and may display the report comprising the ranked list of keywords on a graphical user interface 521 of a display device 121.

The reports generated by the reporting module 114 may, in some embodiments be transmitted by the reporting module 114 to a separate computing device operated by a physician or other healthcare personnel. For example, instead of displaying the report about the keywords associated with the patient on a display system 121 attached to the communication system 101, the report may be transmitted to one or more network accessible computer devices 133a, 133b ... 133n. The network accessible computer devices 133 may be any type of computer system. For example, the network accessible computer systems 133 may be a desktop computer, laptop, tablet, cell phone, smart phone or portable computing device. By transmitting the reports to physicians and other healthcare professions over the network, the physician and employees thereof do not need to be particularly tethered to the computer system 101 generating the report on each patient's keywords and concerns. Delivery to mobile devices may allow for the physician to become mobile and view different patient reports while treating the patients in the physician's office. The reports may be stored, saved and cataloged to a computer readable storage device such as storage device 120 or network repository 140, allowing for the physician to access multiple reports generated by the reporting module and organize each report by date. This may allow for the physician to review old keywords and symptoms and compare the report to the newest assessment of a particular patient, thus gauging the progress of the patient's concerns, whether the concerns are being addressed and to determine if any unaddressed keywords remain that may require the focus of the physician.

Figure 4:
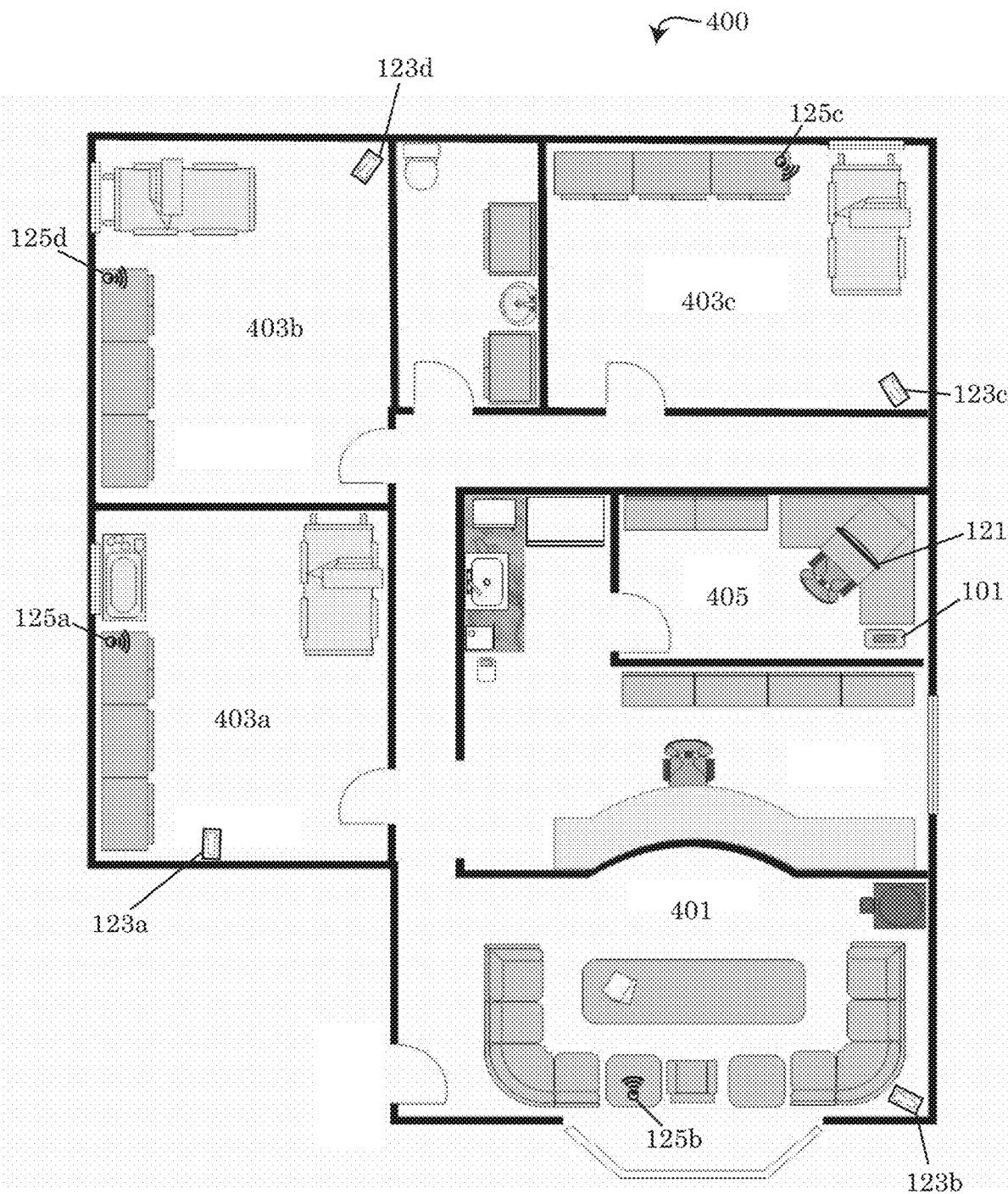
FIG. 4 depicts a schematic view of an embodiment of a healthcare communication system installed in an embodiment of an office environment.

Referring to the drawings, FIG. 4 represents an embodiment of a healthcare communication system 400 which may be installed in a physician's office, hospital or other healthcare treatment facility. As shown in the figure, the communication system 101 and display system 121, may be placed in a separate location from the voice recording system 125 and the video recording system 123. In the example shown, the communication system 101 is placed in the physician's room 405 whereas the plurality of voice recording devices 125a-125d and the video recording devices 123a-123d are placed throughout the office as shown. In the particular system 400 shown in FIG. 4, the voice recording devices 125a-125d and the video recording devices 123a-123d are placed in the waiting room 401 and examination rooms 403a-403c. By having multiple recording devices positioned throughout the office or facility being observed, the patient of interest may be monitored seamlessly as the patient moves and converses with the physician or healthcare providers in the office.

Figure 5:
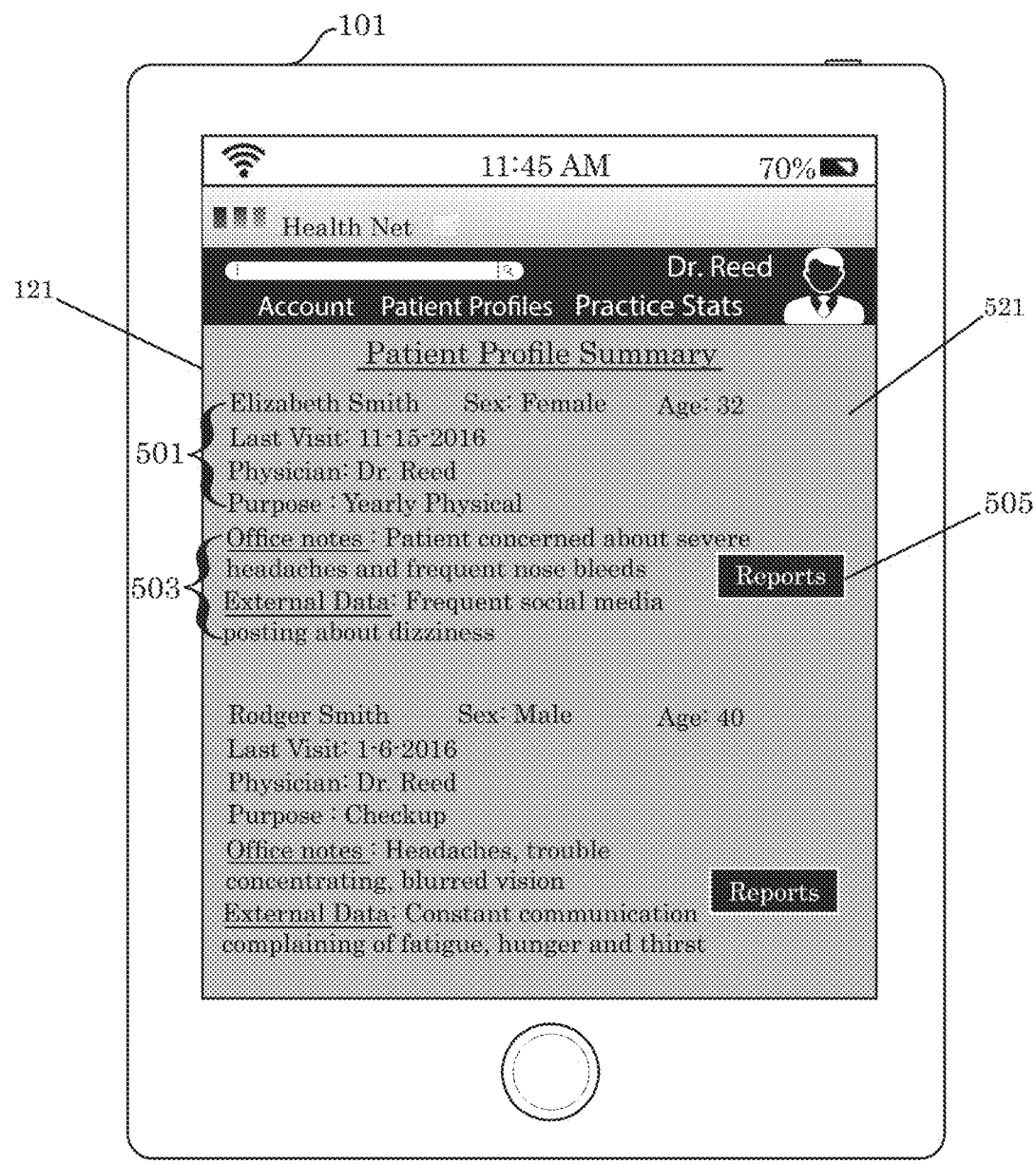
FIG. 5 depicts an embodiment of a computer system displaying a graphical user interface of a healthcare communication system.

Referring to the drawings, FIG. 5 depicts an embodiment of a communication system 101 displaying graphical user interface 521 provided by the communication system 101. The graphical user interface 521 may be accessible by the physician or healthcare personnel that may be responsible for treating the patient being observed by the communication system. Records of each patient may include patient information 501 and one or more notations 503 providing a summary of the patient's concerns both identified by the communication system 101 via voice data as well as from external data obtain from one or more network accessible data sources 131. Embodiments of the graphical user interface (GUI) 521 may allow for a user of GUI 521 to access and query reports 505 generated by the reporting module 114.

Figure 6A:
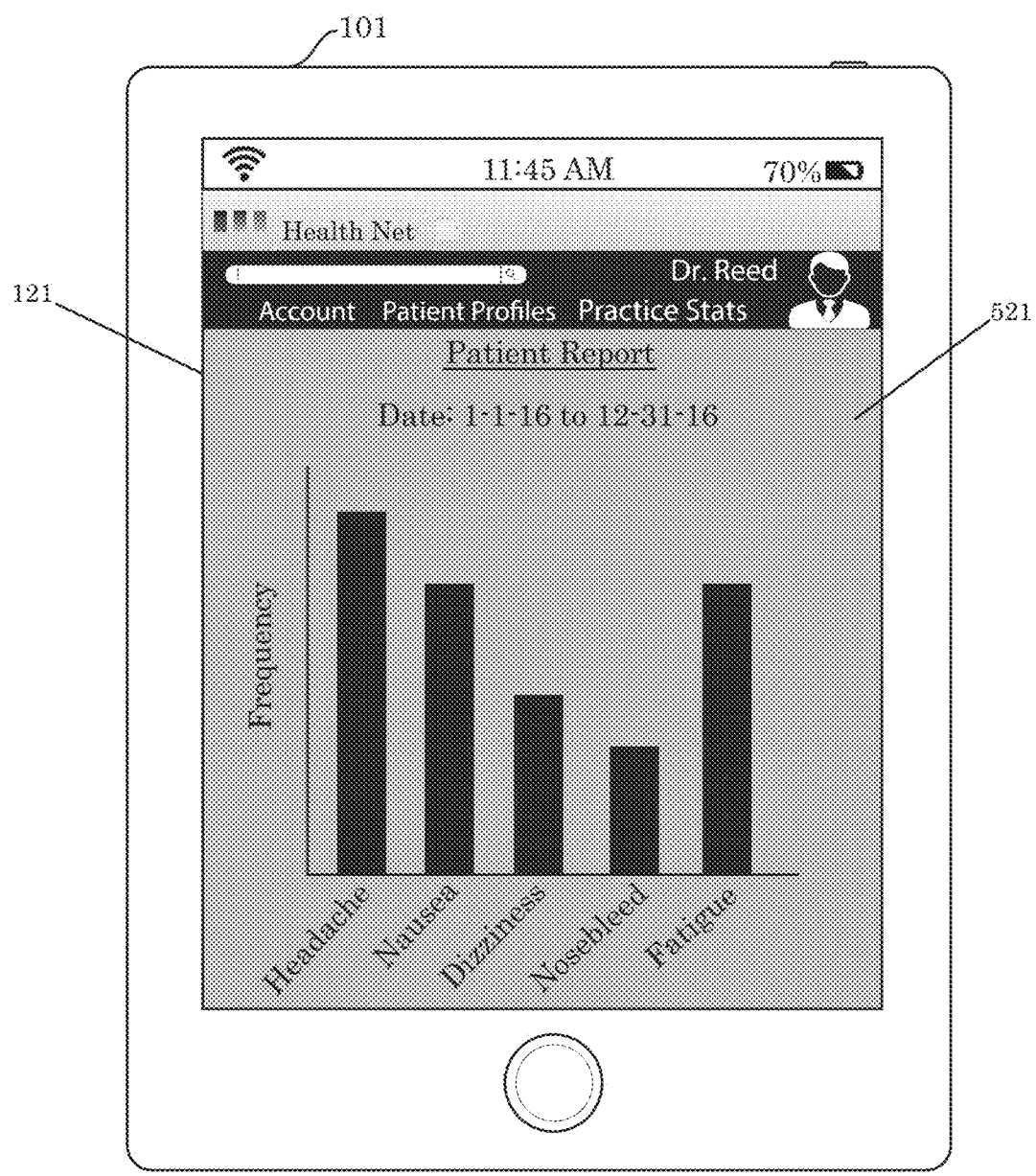
FIG. 6a depicts an embodiment of a computer system displaying a graphical user interface of a healthcare communication system generating an embodiment of a patient report.
Figure 6B:
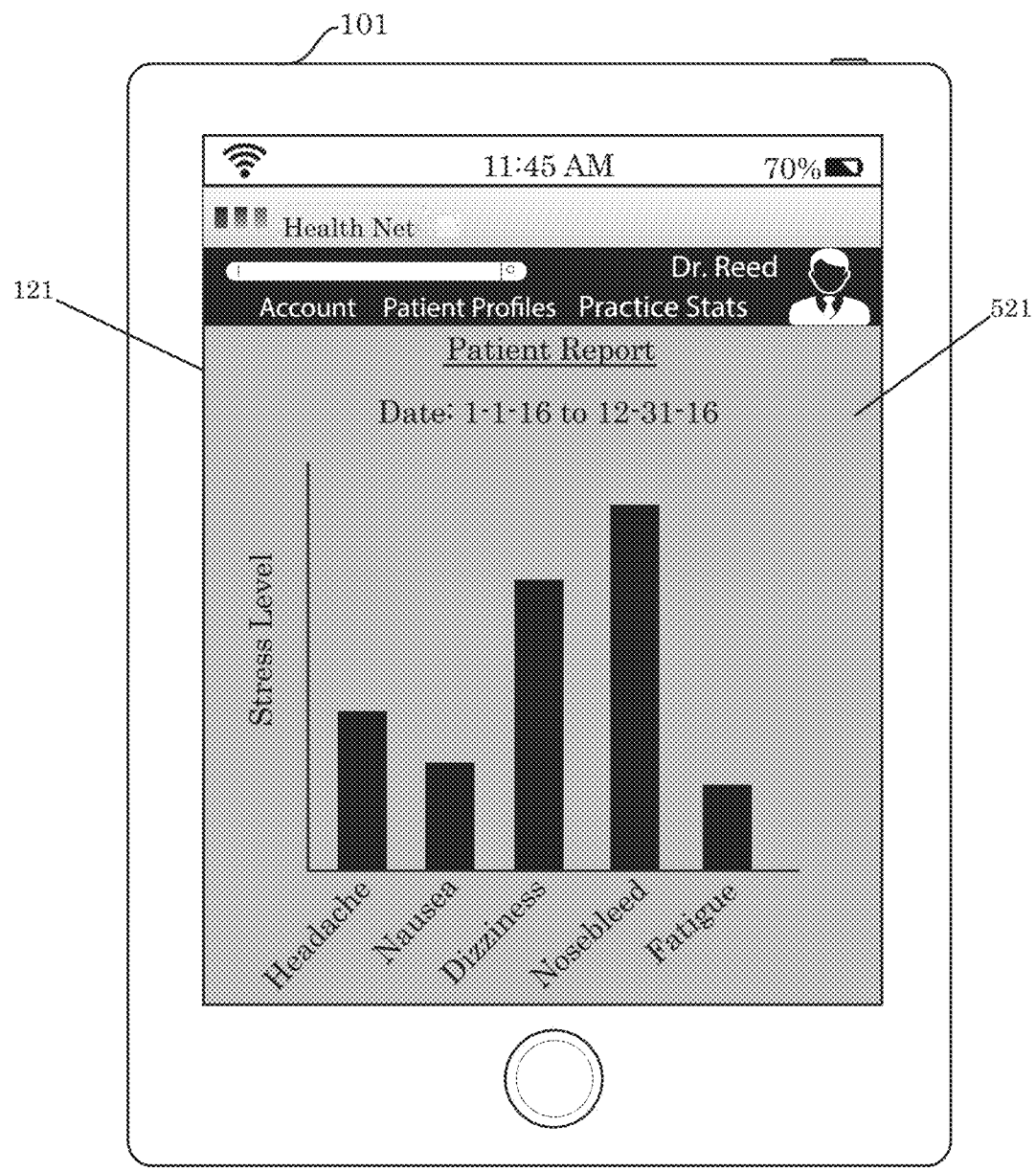
FIG. 6b depicts an embodiment of a computer system displaying a graphical user interface of a healthcare system generating an alternative embodiment of a patient report.

As shown in FIGS. 6a and 6b, the GUI 521 may display one or more different reports 505 comprising one or more ranked lists of keywords derived from the data collected by the communication system 101. For example, in FIG. 6a, a report generated within a particular time frame (year 2016) shows an example of keywords ranked by frequency. The keywords include symptoms such as headache, nausea, dizziness, nosebleed and fatigue, however any keywords may be identified by the communication system 101 as a function of the voice data and data sources 131. As it can be seen by comparing FIG. 6a with 6b, the rankings may change depending on the ranking criteria. As opposed to the ranking of keywords by frequency in FIG. 6a, FIG. 6b depicts an example of a report 505 ranking the identified keywords based on the stress level of the patient. Whereas headaches, nausea and fatigue were the most frequently identified keywords in FIG. 6a, the most stressful keywords as identified by the report of the patient in FIG. 6b were the occurrence of nosebleeds and dizziness. By using multiple ranking systems, a physician may be able to determine which keywords are most important to the patient. In this current example, a physician may have been told about the dizziness and nosebleeds less frequently and thus dismissed or forgot about such symptoms due to the infrequent discussion. The physician, upon viewing the sentiment and stress related to the dizziness and nosebleeds experience by the patient, may choose to focus a discussion with the patient on the identified symptoms causing the patient the most stress.

Figure 7:
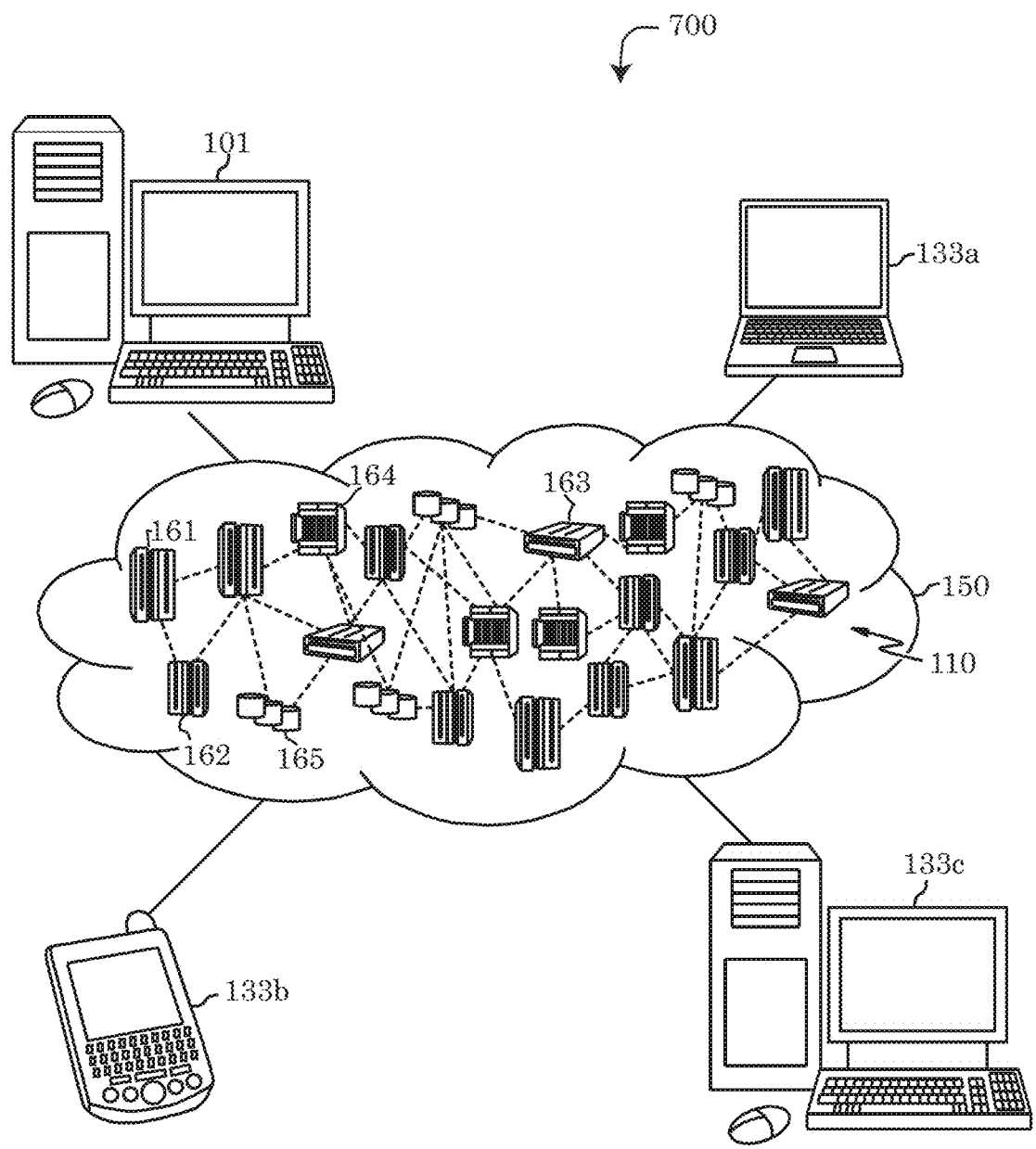
FIG. 7 depicts a cloud computing environment of a healthcare communication system, in accordance with embodiments of the present invention.

FIG. 7 depicts an alternative embodiment of the healthcare communication system 700 wherein the system is operating under a cloud computing model. Cloud computing is a model of service delivery enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. The characteristics of the cloud computing model may be described as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

The service models under a cloud computing environment may be described as follows:

Software as a Service (SaaS): the capability provided to the consumer is to use the provider's applications running on a cloud infrastructure. The applications are accessible from various client devices 101, 133a-133c through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

The deployment models of cloud computing environments may be described as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment may be service oriented with a focus on statelessness, low coupling, modularity, and semantic interoperability. At the heart of cloud computing is an infrastructure that includes a network of interconnected nodes 110.

Referring to the drawings, FIG. 7 is illustrative of a network 130 operating as a cloud computing environment 150. As shown, the cloud computing environment may include one or more cloud computing nodes 110 with which client computing devices 101, 133a-133c used by cloud consumers, such as, for example, desktop computers, laptop computer, mobile devices, tablet computers or cellular telephones may communicate. Computer system nodes 110 may communicate with one another and may be grouped (not shown) physically or virtually, in one or more networks, such as Private, Community, Public, or Hybrid clouds as described hereinabove, or a combination thereof, allowing for the cloud computing environment of the medical network 150 to offer infrastructure, platforms and/or software as services for which a cloud consumer does not need to maintain resources on a local computing device. It is understood that the types of computing devices shown in FIG. 7 are intended to be illustrative only and that nodes 110 and cloud computing environment can communicate with any type of computerized device over any type of network and/or network addressable connection (e.g., using a web browser).

Figure 8:
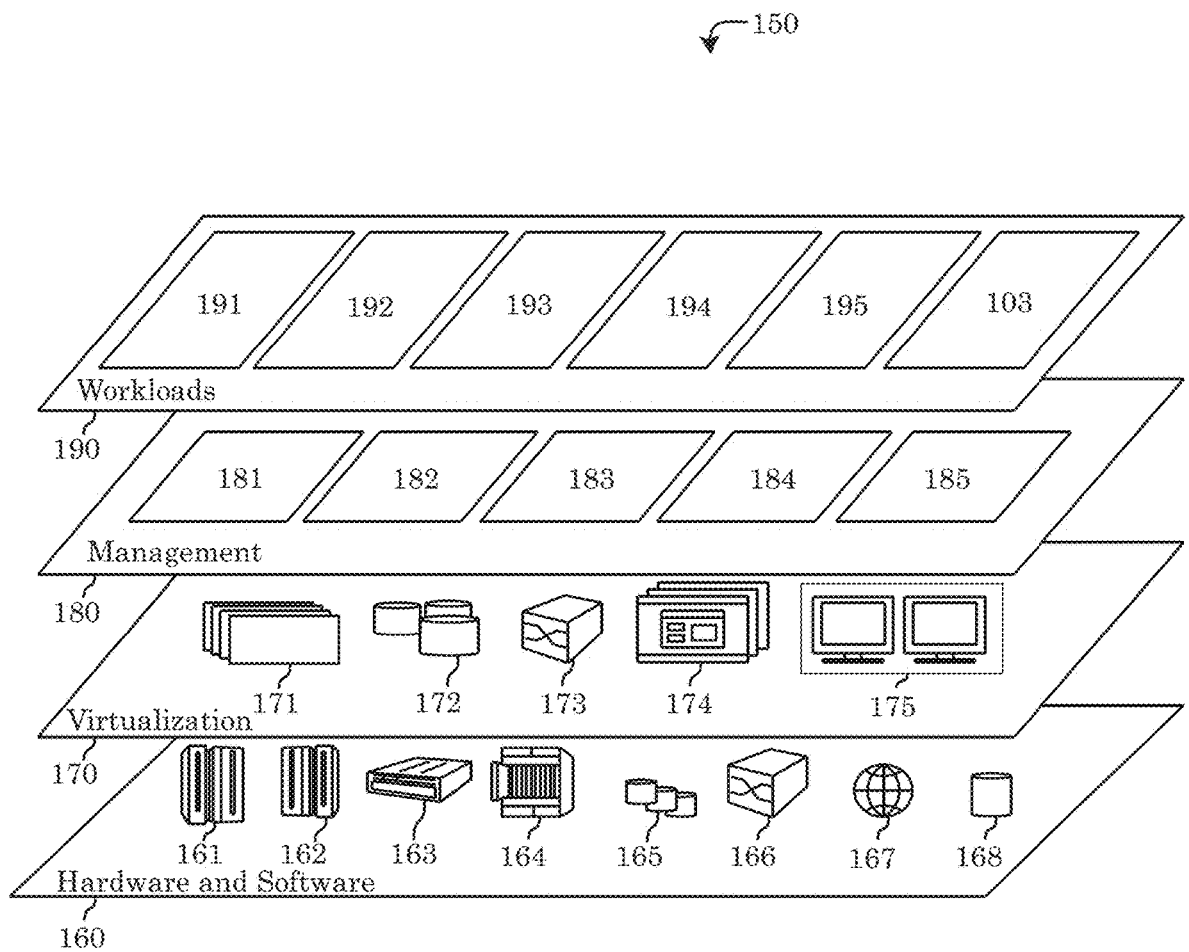
FIG. 8 depicts abstraction model layers of a cloud computing environment of a healthcare communication system, in accordance with embodiments of the present invention

Referring now to FIG. 8, a set of functional abstraction layers provided by a cloud computing environment of the cloud network 150 is shown. It should be understood in advance that the components, layers, and functions shown in FIG. 8 are intended to be illustrative only and embodiments of the invention are not limited thereto. As depicted, the following layers and corresponding functions are provided:

Hardware and software layer 160 includes hardware and software components. Examples of hardware components include: mainframes 161; RISC (Reduced Instruction Set Computer) architecture based servers 162; servers 163; blade servers 164; storage devices 165; and networking components 166. In some embodiments, software components may include network application server software 167 and database software 168.

Virtualization layer 170 provides an abstraction layer from which the following examples of virtual entities may be provided: virtual servers 171; virtual storage 172; virtual networks 173, including virtual private networks; virtual applications and operating systems 174; and virtual clients 175.

Embodiments of the management layer 180 may provide the functions described below. Resource provisioning 181 provides dynamic procurement of computing resources and other resources that are utilized to perform tasks within the cloud computing environment. Metering and Pricing 182 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 183 provides access to the cloud computing environment of the medical network 150 for consumers (i.e. prospective and existing patients) and system administrators. Service level management 184 provides cloud computing resource allocation and management such that required service levels are met. Service Level Agreement (SLA) planning and fulfillment 185 provides pre-arrangement for, and procurement of, cloud computing resources for which a future requirement is anticipated in accordance with an SLA.

Workloads layer 190 provides examples of functionality for which the cloud computing environment may be utilized. Examples of workloads and functions which may be provided from this layer include: records management 191; web page management 192; searching and results management 193; data analytics processing 194; profile management 195; and healthcare communication 103.

Method for Automating Healthcare Communication

Figure 9:
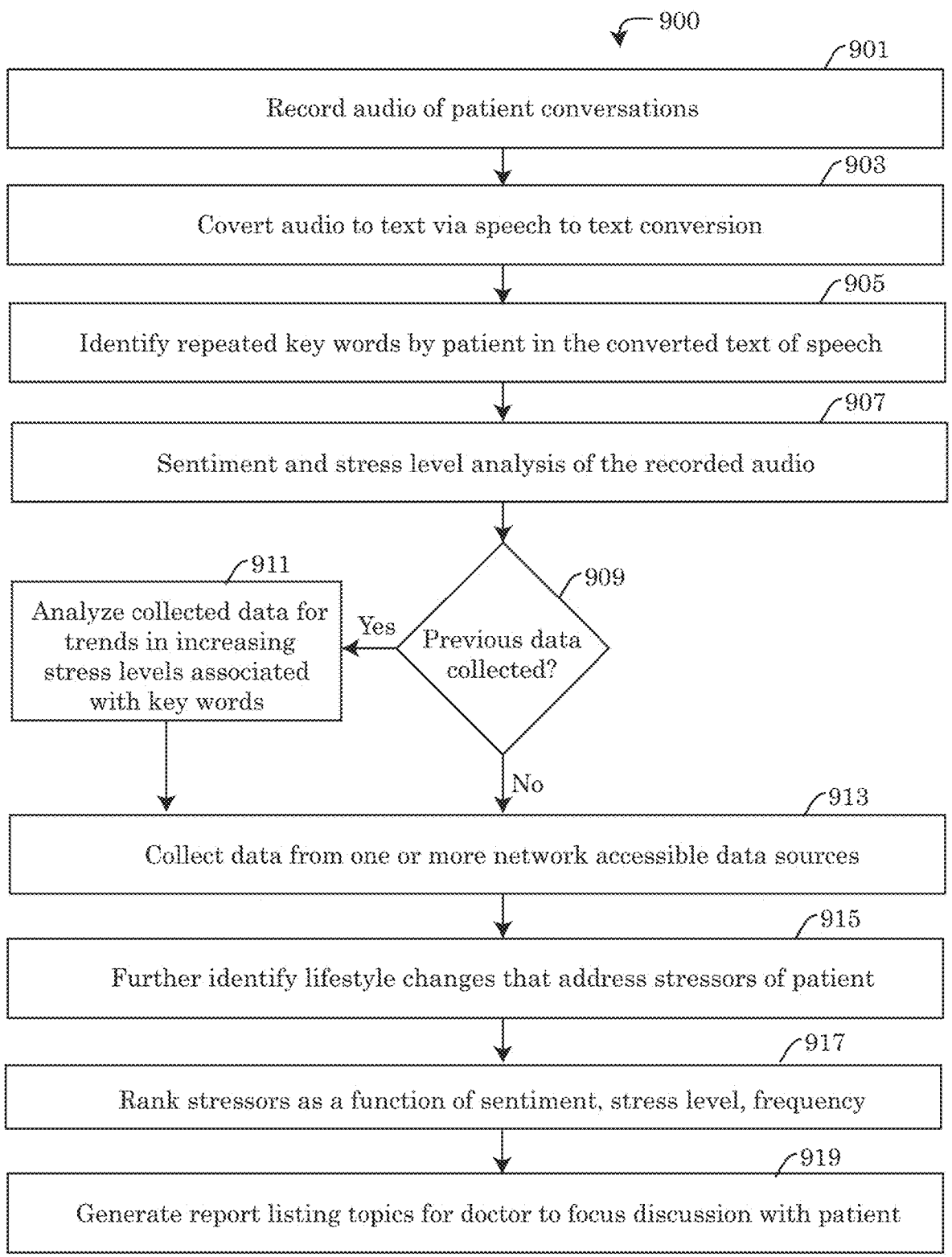
FIG. 9 depicts a flow chart of an embodiment of a method for automating healthcare communication.
Figure 10:
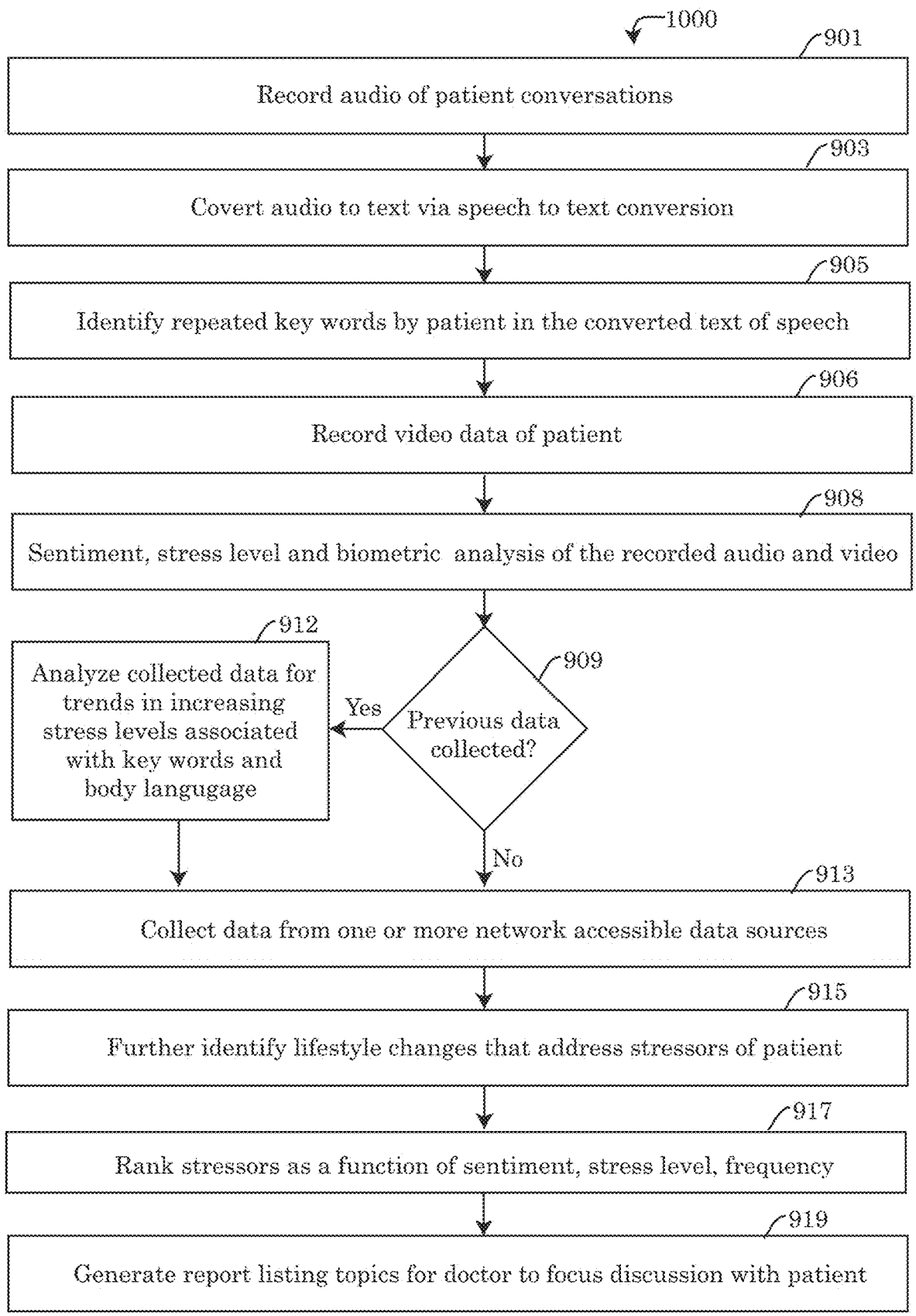
FIG. 10 depicts a flow chart of an alternative embodiment of a method for automating healthcare communication.

The drawing of FIG. 9-10 represents embodiments 900, 1000 of an algorithm that may be implemented for automating healthcare communication, in accordance with the systems described in FIGS. 1-8 using one or more computer systems defined generically in FIG. 11 below, and more specifically by the specific embodiments depicted in FIGS. 1-8. A person skilled in the art should recognize that the steps of the method described in FIGS. 9-10 may not require all of the steps disclosed herein to be performed, nor does the algorithm of FIGS. 9-10 necessarily require that all the steps be performed in the particular order presented. Variations of the method steps presented in FIGS. 9-10 may be performed in a different order than presented by FIGS. 9-10.

The algorithm 900, described in FIG. 9, may initiate at step 901. In step 901, the recording module 105 of the communication system 101 may receive and record audio of patient conversations as voice data. The voice data being recorded may be inputted into one or more recording devices of a voice recording system 125 connected to the communication system 101. The voice data being received by the recording module 105, formatted and stored as a voice recording in the storage device 120 and/or a network accessible storage device such as network repository 140.

In step 903 of method 900, the audio recorded by the voice recording system in step 901 may be converted from audio to text. The voice to text module 107 may receive the voice data and apply one or more speech to text algorithms. Once converted to text, the parsing module 108 may parse the text obtained from the voice to text module 107 in order to identify a series of one or more key words used in audio conversations by the patient. The parsing module may, in some embodiments, identify the frequency of keywords being repeated by the patient.

In step 905 of the algorithm 900, the parsing module 108 may be equipped with a natural language processor. The natural language processor may analyze the keywords and phrases parsed from the outputted text of step 903 for sentiment and stress levels associated with the key words, phrase and thus the recorded voice data's audio. The natural language processor may identify stress variables associated with the patient's key words and identify the patient's mood or attitude at the time the voice data was recorded in step 901. In step 909, the algorithm may further compare the sentiment and stress level of the patient with previously collected data in order to establish one or more trends in the sentiment of the patient when one or more particular keywords are spoken. If, in step 909 there is previous data collected by the communication system 101, the algorithm may proceed to step 911, wherein the previously collected data is analyzed for trends in increasing stress levels between the key words most recently identified in step 905 and previous keywords, otherwise, the algorithm may proceed to step 913.

In step 913, the algorithm 900 may collect additional data from external sources that may not be maintained by communication system 101, such as network accessible data sources 131. The data collection module 109 may scan one or more data sources 131, including social media websites, applications and messaging services for additional data that may be parsed into keywords or provide context for the patient's symptoms or healthcare concerns. In step 915, the data collection module scanning one or more data sources 131 may identify one or more lifestyle changes described by the patient. The lifestyle change or other described matters in the data sources 131 may include information that may not have been conveyed to the physician therefore may influence the ranking of one or more keywords that may be presented to the physician for further discussion between the patient and physician.

In step 917, each of the keywords associated with symptoms, healthcare or medical stressors may be ranked as a function of the patient's sentiment, stress level, frequency and frequency of the keywords being used by the patient when the voice data was recorded by the voice recording system 125 and may be further ranked within the context of additional data collected in step 913. Each of the ranked keywords may, in step 919 be presented to the physician as part of a report generated by the reporting module 114.

Similar to the embodiment of the algorithm 900, the algorithm 1000 presents an alternative method for automating healthcare communication. Similar to algorithm 900, algorithm 1000 performs steps 901-905. In step 906 however, the algorithm 1000 further introduces a step comprising recording video data of the patient. For example using a video recording system 123 connected to the communication system 101. The inclusion of video data may further allow for the communication system 101 to assess the patient's body language during the recordation of the voice data collected in step 901. In step 908, the parsing module 108 and the natural language processor may perform the sentiment analysis and stress level identification of the voice data as previously described in step 907. However in step 908, the communication system 101 may further identify sentiment and stress level in light of a biometric analysis of the body language of the patient displayed by the recorded video data at the time of the recordation of the voice data.

In step 909, the algorithm 1000 may proceed similar to algorithm 900 as described above. However, if in step 909 it is determined that previous data has been collected by communication system, the algorithm 1000 may proceed to step 912 wherein the currently collected data is not only analyzed for trends directed toward increased stress levels associated with the parsed key words of step 905 and 908, but also in view of the body language identified by the communication system during the biometric analysis of the patient while espousing the voice data collected in step 901. Subsequently, the algorithm 1000 may be completed from steps 913 to steps 919 in a manner similar to the algorithm 900 described above.

Computer System

Figure 11:
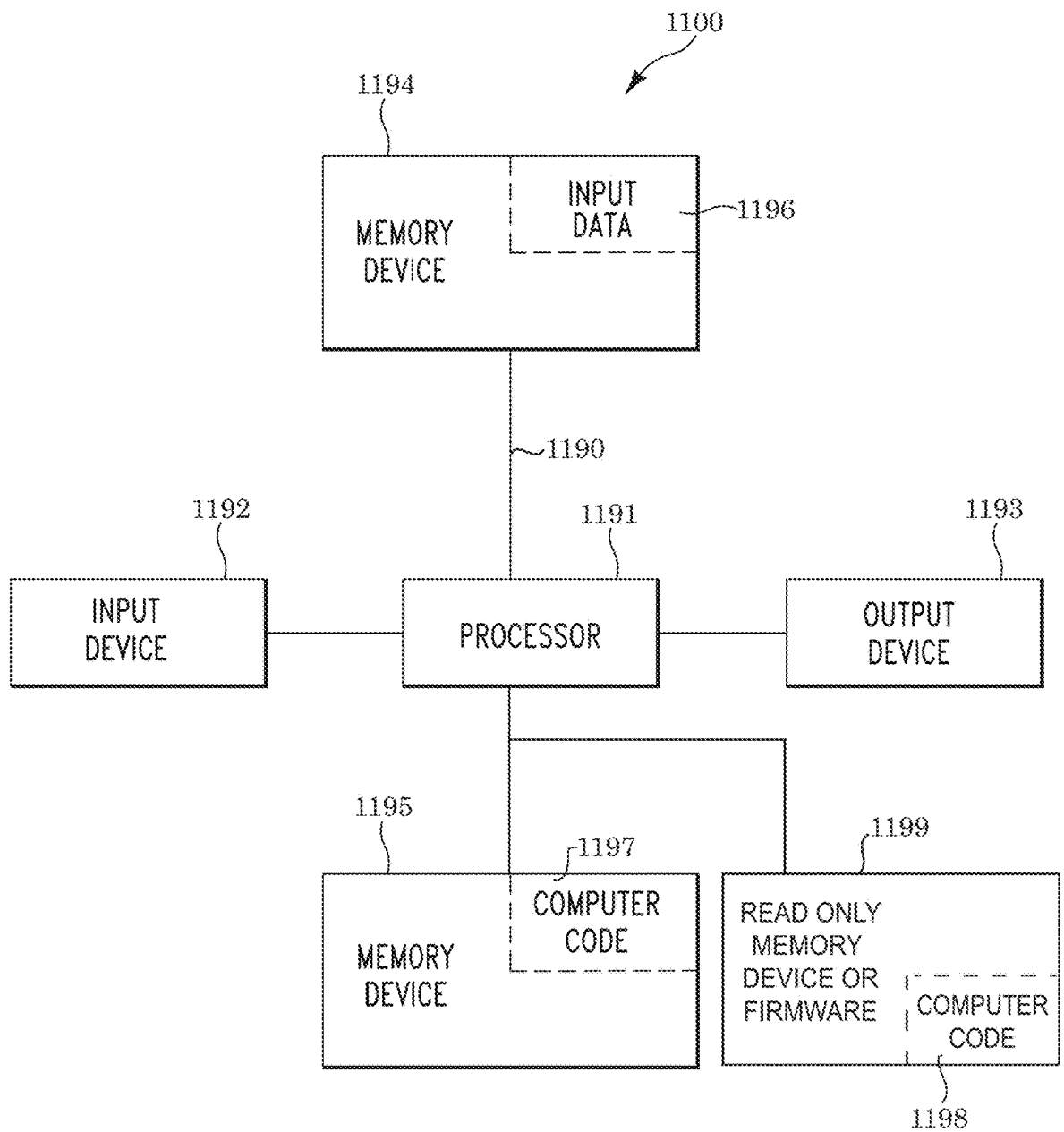
FIG. 11 depicts a block diagram of a computer system for the healthcare communication system of FIG. 1, capable of implementing methods for automating healthcare communication of FIGS. 9-10, in accordance with embodiments of the present invention.

Referring to the drawings, FIG. 11 illustrates a block diagram of a computer system 1100 that may be included in the systems of FIG. 1—and for implementing the methods for automating healthcare communication as described in the algorithms of FIGS. 9-10 and in accordance with the embodiments described in the present disclosure. The computer system 1100 may generally comprise a processor 1191, otherwise referred to as a central processing unit (CPU), an input device 1192 coupled to the processor 1191, an output device 1193 coupled to the processor 1191, and memory devices 1194 and 1195 each coupled to the processor 1191. The input device 1192, output device 1193 and memory devices 1194, 1195 may each be coupled to the processor 1191 via a bus 1190. Processor 1191 may perform computations and control the functions of computer 1100, including executing instructions included in the computer code 1197 for tools and programs for automating healthcare communication, in the manner prescribed by the embodiments of the disclosure using the systems of FIGS. 1-8 wherein the instructions of the computer code 1197 may be executed by processor 1191 via memory device 1195. The computer code 1197 may include software or program instructions that may implement one or more algorithms for implementing the methods for automating healthcare communication, as described in detail above and in FIGS. 9-10. The processor 1191 executes the computer code 1197. Processor 1191 may include a single processing unit, or may be distributed across one or more processing units in one or more locations (e.g., on a client and server).

The memory device 1194 may include input data 1196. The input data 1196 includes any inputs required by the computer code 1197, 1198. The output device 1193 displays output from the computer code 1197, 1198. Either or both memory devices 1194 and 1195 may be used as a computer usable storage medium (or program storage device) having a computer readable program embodied therein and/or having other data stored therein, wherein the computer readable program comprises the computer code 1197, 1198. Generally, a computer program product (or, alternatively, an article of manufacture) of the computer system 1100 may comprise said computer usable storage medium (or said program storage device).

Memory devices 1194, 1195 include any known computer readable storage medium, including those described in detail below. In one embodiment, cache memory elements of memory devices 1194, 1195 may provide temporary storage of at least some program code (e.g., computer code 1197, 1198) in order to reduce the number of times code must be retrieved from bulk storage while instructions of the computer code 1197, 1198 are executed. Moreover, similar to processor 1191, memory devices 1194, 1195 may reside at a single physical location, including one or more types of data storage, or be distributed across a plurality of physical systems in various forms. Further, memory devices 1194, 1195 can include data distributed across, for example, a local area network (LAN) or a wide area network (WAN). Further, memory devices 1194, 1195 may include an operating system (not shown) and may include other systems not shown in the figures.

In some embodiments, rather than being stored and accessed from a hard drive, optical disc or other writeable, rewriteable, or removable hardware memory device 1194, 1195, stored computer program code 1198 (e.g., including algorithms) may be stored on a static, non-removable, read-only storage medium such as a Read-Only Memory (ROM) device 1199, or may be accessed by processor 1191 directly from such a static, non-removable, read-only medium 1199. Similarly, in some embodiments, stored computer program code 1197 may be stored as computer-readable firmware 1199, or may be accessed by processor 1191 directly from such firmware 1199, rather than from a more dynamic or removable hardware data-storage device 1195, such as a hard drive or optical disc.

In some embodiments, the computer system 1100 may further be coupled to an input/output (I/O) interface (for example I/O interface 117) and a computer data storage unit (for example a data store, data mart or repository). An I/O interface may include any system for exchanging information to or from an input device 1192 or output device 1193. The input device 1192 may be, inter alia, a keyboard, joystick, trackball, touchpad, scanning device, bar code reader, mouse, sensors, beacons, RFID tags, microphones, recording device, biometric input device, camera, timer, etc. The output device 1193 may be, inter alia, a printer, a plotter, a display device (such as a computer screen or monitor), a magnetic tape, a removable hard disk, a floppy disk, etc. The memory devices 1194 and 1195 may be, inter alia, a hard disk, a floppy disk, a magnetic tape, an optical storage such as a compact disc (CD) or a digital video disc (DVD), a dynamic random access memory (DRAM), a read-only memory (ROM), etc. The bus 1190 may provide a communication link between each of the components in computer 1100, and may include any type of transmission link, including electrical, optical, wireless, etc.

The I/O interface may allow computer system 1100 to store information (e.g., data or program instructions such as program code 1197, 1198) on and retrieve the information from a computer data storage unit (not shown). Computer data storage units include any known computer-readable storage medium, which is described below. In one embodiment, computer data storage unit may be a non-volatile data storage device, such as a magnetic disk drive (i.e., hard disk drive) or an optical disc drive (e.g., a CD-ROM drive which receives a CD-ROM disk).

As will be appreciated by one skilled in the art, in a first embodiment, the present invention may be a method; in a second embodiment, the present invention may be a system; and in a third embodiment, the present invention may be a computer program product. Any of the components of the embodiments of the present invention can be deployed, managed, serviced, etc. by a service provider able to deploy or integrate computing infrastructure with respect to automating healthcare communication. Thus, an embodiment of the present invention discloses a process for supporting computer infrastructure, where the process includes providing at least one support service for at least one of integrating, hosting, maintaining and deploying computer-readable code (e.g., program code 1197, 1198) in a computer system (e.g., computer 1100) including one or more processor(s) 1191, wherein the processor(s) carry out instructions contained in the computer code 1197 causing the computer system to automate healthcare communication. Another embodiment discloses a process for supporting computer infrastructure, where the process includes integrating computer-readable program code into a computer system including a processor.

The step of integrating includes storing the program code in a computer-readable storage device of the computer system through use of the processor. The program code, upon being executed by the processor, implements a method for automating healthcare communication as described in this application. Thus the present invention discloses a process for supporting, deploying and/or integrating computer infrastructure, integrating, hosting, maintaining, and deploying computer-readable code into the computer system 1100, wherein the code in combination with the computer system 1100 is capable of performing a method for automating healthcare communication between a patient and healthcare provider.

A computer program product of the present invention comprises one or more computer readable hardware storage devices having computer readable program code stored therein, said program code containing instructions executable by one or more processors of a computer system to implement the methods of the present invention.

A computer program product of the present invention comprises one or more computer readable hardware storage devices having computer readable program code stored therein, said program code containing instructions executable by one or more processors of a computer system to implement the methods of the present invention.

A computer system of the present invention comprises one or more processors, one or more memories, and one or more computer readable hardware storage devices, said one or more hardware storage devices containing program code executable by the one or more processors via the one or more memories to implement the methods of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer system comprising
a processor;
a memory device coupled to the processor;
a digital audio recording system;
a video recording system having a camera system; and
a computer readable storage device coupled to the processor, wherein the storage device contains program code executable by the processor via the memory device to implement a method for automating healthcare communication comprising the steps of:
   detecting, by said processor via said digital audio recording system, audible sounds from a plurality of audio recording devices positioned throughout facilities of a physician;
   enabling, by said processor in response to said detecting said audible sounds, recording functionality of said digital audio recording system;
   receiving, by the processor in response to said detecting and said enabling, voice data of a patient communicating with various personnel of said facilities recorded by the digital audio recording system from a continuous audio stream;
   detecting, by said processor, human voice variables within said voice data;
   converting, by the processor, the voice data to text, wherein said converting comprises:
      translating an analog wave recorded by a microphone of the digital audio recording system into digital data via execution of an analog-to-digital converter by digitizing speech of the voice data via determined measurements of the analog wave with respect to a series of intervals;
      removing unwanted background noise from said digital data; and
      separating sounds of said digital data into different bands of frequency;
   parsing, by the processor, the text of the voice data for key words, wherein said parsing comprises:
      reading, via a specialized scanner component of said computing system, the text being parsed one character, of characters, at a time;
      transforming, by a specialized lexer component of said computing system, a stream of characters into a stream of tokens;
      reading, by a specialized parser component of said computing system, the stream of tokens;
      building a parse tree based on the stream of tokens and in accordance with language rule code; and
      identifying, one or more associated key words or phrases associated with a specified frequency of usage;
   analyzing, by the processor based on said human voice variables, the voice data for sentiment and stress variables with respect to said specified frequency of usage thereby indicating a heightened stress of the patient;
   further analyzing, by the processor, video data of the patient recorded by a video recording system for additional evidence of the sentiment and stress variables further corresponding to the heightened sense of stress of the patient identified in the voice data, wherein said further analyzing comprises:
      enabling, by said processor in response to said detecting movement of said patient, recording functionality of said video recording system comprising a plurality of video recording devices positioned throughout said facilities of said physician;
      detecting, by said processor via said video recording system, visual cues of body language of said patient communicating with said various personnel of said facilities; and
      identifying, tracking, and emphasizing, by said processor based on said visual cues, symptoms and concerns of said patient with respect to an importance to said physician;
   ranking, by the processor, the key words as a function of the sentiment and stress variables analyzed with respect to the video data and the voice data;
   generating, by the processor, a list corresponding to the ranking of the key words; and
   enabling, by said processor, said physician to review said list thereby enabling said physician to initiate communication with said patient for resolving the heightened sense of stress of the patient with respect to medical symptoms.

2. The computer system of claim 1, wherein the method of automating healthcare communication further comprises the steps of:
   retrieving, by the processor, patient data from one or more network accessible data sources; and
   further analyzing, by the processor, the sentiment and stress variables indicating the heightened sense of stress of the patient as a function of the patient data retrieved from the one or more network accessible data sources.

3. The computer system of claim 2, wherein the one or more network accessible data sources is a social media website.

4. The computer system of claim 1, wherein the list generated by the processor comprises said one or more keywords organized by frequency of the key word within a specified time frame or as a function of a stress level of the patient providing the voice data comprising the key words.

5. A computer program product, comprising a computer readable hardware storage device storing a computer readable program code, the computer readable program code comprising an algorithm that when executed by a computer processor of a computing system implements a method for automating healthcare communication, the method comprising the steps of:
   detecting, by said processor via said digital audio recording system, audible sounds from a plurality of audio recording devices positioned throughout facilities of a physician;
   enabling, by said processor in response to said detecting said audible sounds, recording functionality of said digital audio recording system;
   receiving, by said processor in response to said detecting and said enabling, voice data of a patient communicating with various personnel of said facilities recorded by said digital voice recording system from a continuous audio stream;
   detecting, by said processor, human voice variables within said voice data;
   converting, by the processor, the voice data to text, wherein said converting comprises:

translating an analog wave recorded by a microphone of the digital audio recording system into digital data via execution of an analog-to-digital converter by digitizing speech of the voice data via determined measurements of the analog wave with respect to a series of intervals; and removing unwanted background noise from said digital data; and separating sounds of said digital data into different bands of frequency;

parsing, by the processor, the text of the voice data for key words, wherein said parsing comprises:

reading, via a specialized scanner component of said computing system, the text being parsed one character, of characters, at a time;

transforming, by a specialized lexer component of said computing system, a stream of characters into a stream of tokens;

reading, by a specialized parser component of said computing system, the stream of tokens;

building a parse tree based on the stream of tokens and in accordance with language rule code; and identifying, one or more associated key words or phrases associated with a specified frequency of usage;

analyzing, by the processor based on said human voice variables, the voice data for sentiment and stress variables with respect to said specified frequency of usage thereby indicating a heightened stress of the patient;

further analyzing, by the processor, video data of the patient recorded by the video recording system for additional evidence of the sentiment and stress variables further corresponding to the heightened sense of stress of the patient identified in the voice data, wherein said further analyzing comprises:

enabling, by said processor in response to said detecting movement of said patient, recording functionality of said video recording system comprising a plurality of video recording devices positioned throughout said facilities of said physician;

detecting, by said processor via said video recording system, visual cues of body language of said patient communicating with said various personnel of said facilities; and identifying, tracking, and emphasizing, by said processor based on said visual cues, symptoms and concerns of said patient with respect to an importance to said physician;

ranking, by the processor, the key words as a function of the sentiment and stress variables analyzed with respect to the video data and the voice data;

generating, by the processor, a list corresponding to the ranking of the key words; and enabling, by said processor, said physician to review said list thereby enabling said physician to initiate communication with said patient for resolving the heightened sense of stress of the patient with respect to medical symptoms.

6. The computer program product of claim 5, wherein the algorithm further comprises:

retrieving, by the processor, patient data from one or more network accessible data sources; and further analyzing, by the processor, the sentiment and stress variables indicating the heightened sense of stress of the patient as a function of the patient data retrieved from the one or more network accessible data sources.

7. The computer program product of claim 6, wherein the one or more network accessible data sources is a social media website.

8. The computer program product of claim 5, wherein the list generated by the processor comprises one or more keywords organized by frequency of the key word in the text of the voice data or as a function of a stress level of the patient providing the voice data comprising the key words.

9. The computer program product of claim 5, wherein the algorithm further comprises:

further receiving, by the processor, video data of the patient recorded by a video recording system;

further analyzing, by the processor, the video data for additional evidence of sentiment and stress variables further corresponding to the heightened sense of stress of the patient identified in the voice data.

10. A computer system comprising:

a processor;

a memory device coupled to the processor;

a digital audio recording system;

a video recording system having a camera system; and a computer readable storage device coupled to the processor, wherein the storage device contains program code executable by the processor via the memory device to implement a method for automating healthcare communication comprising the steps of:

detecting, by said processor via said digital audio recording system, audible sounds from a plurality of audio recording devices positioned throughout facilities of a physician;

enabling, by said processor in response to said detecting said audible sounds, recording functionality of said digital audio recording system;

receiving, by the processor in response to said detecting, voice data of a patient communicating with various personnel of said facilities recorded by the digital audio recording system from a continuous audio stream;

detecting, by said processor, human voice variables within said voice data;

converting, by the processor, the voice data to text, wherein said converting comprises:

translating an analog wave recorded by a microphone of the digital audio recording system into digital data via execution of an analog-to-digital converter by digitizing speech of the voice data via determined measurements of the analog wave with respect to a series of intervals; and removing unwanted background noise from said digital data; and separating sounds of said digital data into different bands of frequency;

parsing, by the processor, the text of the voice data for key words, wherein said parsing comprises:

reading, via a specialized scanner component of said computing system, the text being parsed one character, of characters, at a time;

transforming, by a specialized lexer component of said computing system, a stream of characters into a stream of tokens;

reading, by a specialized parser component of said computing system, the stream of tokens;

building a parse tree based on the stream of tokens and in accordance with language rule code; and identifying, one or more associated key words or phrases associated with a specified frequency of usage;

further receiving, by the processor, video data of the patient recorded by a video recording system, wherein said further receiving comprises:
  enabling, by said processor is response to said detecting movement of said patient, recording functionality of said video recording system comprising a plurality of video recording devices positioned throughout said facilities of said physician;
  detecting, by said processor via said video recording system, visual cues of body language of said patient communicating with said various personnel of said facilities; and
  identifying, tracking, and emphasizing, by said processor based on said visual cues, symptoms and concerns of said patient with respect to an importance to said physician;
tagging, by the processor, the video data of the patient with one or more tagged key words;
analyzing, by the processor based on said human voice variables, the voice data for sentiment and stress variables with respect to said specified frequency of usage thereby indicating a heightened stress of the patient;
ranking, by the processor, the key words and tagged key words as a function of the sentiment and stress variables identified during the analyzing step;
generating, by the processor, a list corresponding to the ranking of the key words;
displaying, by the processor, the list generated by the processor on a graphical user interface; and
enabling, by said processor, said physician to review said list thereby enabling said physician to initiate communication with said patient for resolving the heightened sense of stress of the patient with respect to medical symptoms.

11. The computer system of claim 10, further comprising:
retrieving, by the processor, patient data from one or more network accessible data sources;
further analyzing, by the processor, the sentiment and stress variables indicating the heightened sense of stress of the patient as a function of the patient data retrieved from the one or more network accessible data sources.

12. The computer system of claim 11, wherein the one or more network accessible data sources is a social media website.

13. The computer system of claim 10, wherein the list generated by the processor comprises the one or more keywords and one or more tagged key words organized by frequency of use within a specified time frame or as a function of a stress level of the patient.

14. The computer system of claim 10, wherein the audio recording system and the video recording system wirelessly communicate with the processor via a wireless network connection.

\* \* \* \* \*